(12) United States Patent
Christie et al.

(10) Patent No.: US 10,335,163 B2
(45) Date of Patent: Jul. 2, 2019

(54) POLYMER 4-IN-2 FEMORAL CUTTING INSTRUMENT HAVING SEPARABLE A/P AND CHAMFER CUTTING BLOCKS

(71) Applicant: DEPUY IRELAND UNLIMITED COMPANY, Ringaskiddy, Co Cork OT (IE)

(72) Inventors: Charles D. Christie, Warsaw, IN (US); Duncan G. Young, Yorkshire (GB); Jon M. Edwards, Warsaw, IN (US); Hasib Mohammed, Okemos, MI (US)

(73) Assignee: DEPUY IRELAND UNLIMITED COMPANY, Ringaskiddy, Co Cork (IE)

( * ) Notice: Subject to any disclaimer, the term of this patent is extended or adjusted under 35 U.S.C. 154(b) by 1324 days.

(21) Appl. No.: 13/785,305

(22) Filed: Mar. 5, 2013

(65) Prior Publication Data
US 2014/0257300 A1    Sep. 11, 2014

(51) Int. Cl.
*A61B 17/15* (2006.01)
*A61B 17/14* (2006.01)
*A61B 17/00* (2006.01)
*A61B 17/16* (2006.01)

(52) U.S. Cl.
CPC ............ *A61B 17/155* (2013.01); *A61B 17/14* (2013.01); *A61B 17/154* (2013.01); *A61B 17/164* (2013.01); *A61B 17/1615* (2013.01); *A61B 2017/0023* (2013.01)

(58) Field of Classification Search
CPC ... A61B 17/151; A61B 17/154; A61B 17/155; A61B 17/15; A61B 2017/0023

USPC ....................... 606/87–89; 403/195; 411/907
See application file for complete search history.

(56) References Cited

U.S. PATENT DOCUMENTS

| | | | |
|---|---|---|---|
| 2,181,746 A | 11/1939 | Siebrandt et al. | |
| 3,835,849 A | 9/1974 | Mc Guire et al. | |
| 4,191,861 A | 3/1980 | Walker | |
| D260,927 S | 9/1981 | Glenn | |
| D281,622 S | 12/1985 | Diamond | |
| 4,565,192 A | 1/1986 | Shapiro et al. | |
| 4,633,862 A | 1/1987 | Petersen | |
| 4,692,073 A | 9/1987 | Martindell et al. | |
| 4,718,413 A * | 1/1988 | Johnson ............... | A61B 17/157 606/82 |
| 5,002,547 A | 3/1991 | Poggie et al. | |

(Continued)

FOREIGN PATENT DOCUMENTS

| | | |
|---|---|---|
| CN | 101259044 A | 9/2008 |
| CN | 101484085 A | 7/2009 |

(Continued)

OTHER PUBLICATIONS

European Search Report and Opinion for App. No. 14157147.1-1654, dated Apr. 15, 2014.

(Continued)

*Primary Examiner* — Eric S Gibson
*Assistant Examiner* — Marcela I Shirsat
(74) *Attorney, Agent, or Firm* — Barnes & Thornburg LLP

(57) ABSTRACT

An orthopedic surgical instrument includes a polymer 4-in-2 cutting instrument having a number of metallic cutting guides secured thereto. An A/P femoral cutting block of the instrument is removably secured to the instrument's chamfer femoral cutting block.

8 Claims, 11 Drawing Sheets

(56) References Cited

U.S. PATENT DOCUMENTS

| | | | |
|---|---|---|---|
| 5,021,055 A | 6/1991 | Burkinshaw et al. | |
| 5,108,401 A | 4/1992 | Insall et al. | |
| 5,116,338 A | 5/1992 | Poggie et al. | |
| 5,129,907 A | 7/1992 | Heldreth et al. | |
| 5,129,908 A | 7/1992 | Petersen et al. | |
| 5,147,365 A | 9/1992 | Whitlock et al. | |
| 5,174,693 A | 12/1992 | Lee et al. | |
| 5,222,955 A | 6/1993 | Mikhail et al. | |
| 5,250,050 A | 10/1993 | Poggie et al. | |
| 5,258,032 A | 11/1993 | Bertin et al. | |
| 5,284,482 A | 2/1994 | Mikhail et al. | |
| 5,284,485 A | 2/1994 | Kammerer et al. | |
| 5,312,409 A | 5/1994 | McLaughlin et al. | |
| 5,382,254 A | 1/1995 | McGarry et al. | |
| 5,415,663 A | 5/1995 | Luckman et al. | |
| 5,470,328 A | 11/1995 | Furnish et al. | |
| 5,484,451 A | 1/1996 | Akopov et al. | |
| D367,531 S | 2/1996 | Price et al. | |
| 5,499,984 A * | 3/1996 | Steiner | A61B 17/164 408/713 |
| 5,520,692 A | 5/1996 | Ferrante et al. | |
| 5,536,271 A | 7/1996 | Daly et al. | |
| 5,542,947 A | 8/1996 | Treacy | |
| D373,635 S | 9/1996 | Price et al. | |
| 5,575,793 A | 11/1996 | Carls et al. | |
| 5,582,615 A | 12/1996 | Foshee et al. | |
| 5,593,450 A | 1/1997 | Scott et al. | |
| 5,611,802 A | 3/1997 | Samuelson et al. | |
| 5,626,607 A | 5/1997 | Malecki et al. | |
| 5,667,512 A | 9/1997 | Johnson | |
| 5,683,398 A * | 11/1997 | Carls | A61B 17/155 606/82 |
| 5,716,360 A | 2/1998 | Baldwin et al. | |
| 5,716,361 A | 2/1998 | Masini et al. | |
| 5,716,362 A | 2/1998 | Treacy | |
| 5,827,279 A | 10/1998 | Hughett et al. | |
| 5,941,884 A | 8/1999 | Corvelli et al. | |
| 5,944,723 A | 8/1999 | Colleran et al. | |
| 5,957,926 A | 9/1999 | Masini et al. | |
| 5,968,051 A | 10/1999 | Luckman et al. | |
| 6,007,537 A * | 12/1999 | Burkinshaw | A61B 17/155 606/66 |
| 6,010,509 A | 1/2000 | Delgado et al. | |
| 6,056,754 A | 5/2000 | Haines et al. | |
| 6,074,425 A | 6/2000 | Pappas | |
| 6,080,162 A | 6/2000 | Dye et al. | |
| 6,190,391 B1 | 2/2001 | Stubbs | |
| 6,205,884 B1 | 3/2001 | Foley et al. | |
| D459,474 S | 6/2002 | Bratt et al. | |
| 6,419,675 B1 | 7/2002 | Gallo, Sr. | |
| D463,550 S | 9/2002 | Sherman | |
| 6,551,316 B1 | 4/2003 | Rinner et al. | |
| 6,589,248 B1 | 7/2003 | Hughes | |
| 6,851,150 B2 | 2/2005 | Chiang | |
| 6,854,919 B2 * | 2/2005 | Neumann | B25G 1/04 15/145 |
| 6,855,150 B1 | 2/2005 | Linehan | |
| 6,866,667 B2 | 3/2005 | Wood et al. | |
| 6,905,514 B2 | 6/2005 | Carignan et al. | |
| D549,331 S | 8/2007 | Tomatsu et al. | |
| 7,344,540 B2 | 3/2008 | Smucker et al. | |
| 7,356,902 B2 | 4/2008 | Snider et al. | |
| 7,566,335 B1 | 7/2009 | Scott et al. | |
| 7,632,279 B2 | 12/2009 | Bastian | |
| 7,780,594 B2 | 8/2010 | Hutton | |
| 7,806,899 B2 | 10/2010 | Hogg et al. | |
| 7,878,989 B2 | 2/2011 | McMinn | |
| 7,891,071 B2 | 2/2011 | Collazo | |
| D634,011 S | 3/2011 | Phillips et al. | |
| D638,541 S | 5/2011 | Claypool | |
| 7,951,151 B2 * | 5/2011 | Butler | A61B 17/7059 606/280 |
| 7,972,383 B2 | 7/2011 | Goldstein et al. | |
| D642,678 S | 8/2011 | Dockstader et al. | |
| D646,389 S | 10/2011 | Claypool et al. | |
| 8,216,242 B2 | 7/2012 | Marchyn et al. | |
| 8,834,574 B2 | 9/2014 | Todd et al. | |
| 8,951,262 B2 | 2/2015 | Kecman et al. | |
| 9,033,989 B2 * | 5/2015 | Wolfson | A61B 17/155 606/87 |
| 9,125,749 B2 | 9/2015 | Amirouche et al. | |
| 2002/0115987 A1 | 8/2002 | Hildwein et al. | |
| 2003/0069586 A1 | 4/2003 | Errico et al. | |
| 2003/0163137 A1 | 8/2003 | Smucker et al. | |
| 2004/0153066 A1 | 8/2004 | Coon et al. | |
| 2004/0162561 A1 | 8/2004 | Marchyn et al. | |
| 2005/0240196 A1 | 10/2005 | Davis et al. | |
| 2006/0058886 A1 | 3/2006 | Wozencroft | |
| 2006/0142777 A1 | 6/2006 | Bastian | |
| 2007/0118141 A1 | 5/2007 | Marchyn et al. | |
| 2007/0150066 A1 | 6/2007 | McMinn | |
| 2007/0162031 A1 | 7/2007 | Hogg et al. | |
| 2007/0177394 A1 | 8/2007 | Vock et al. | |
| 2007/0179626 A1 | 8/2007 | de la Barrera et al. | |
| 2007/0233142 A1 | 10/2007 | Oliver | |
| 2007/0260227 A1 | 11/2007 | Phan | |
| 2008/0097450 A1 | 4/2008 | Brown et al. | |
| 2008/0114366 A1 | 5/2008 | Smucker et al. | |
| 2008/0154269 A1 | 6/2008 | Roger | |
| 2008/0177394 A1 | 7/2008 | Chauhan | |
| 2008/0221569 A1 | 9/2008 | Moore et al. | |
| 2008/0228190 A1 | 9/2008 | Sherry et al. | |
| 2008/0306484 A1 | 12/2008 | Coon et al. | |
| 2009/0082774 A1 * | 3/2009 | Oti | A61B 17/15 606/87 |
| 2009/0088753 A1 | 4/2009 | Aram et al. | |
| 2009/0264737 A1 | 10/2009 | Haechler et al. | |
| 2009/0326661 A1 | 12/2009 | Wright et al. | |
| 2010/0030223 A1 | 2/2010 | Keller | |
| 2010/0121389 A1 | 5/2010 | Librot et al. | |
| 2010/0152742 A1 | 6/2010 | Nevels et al. | |
| 2010/0160924 A1 | 6/2010 | Soliman | |
| 2010/0168752 A1 | 7/2010 | Edwards | |
| 2010/0168753 A1 | 7/2010 | Edwards et al. | |
| 2010/0204701 A1 | 8/2010 | Tallarida et al. | |
| 2010/0249938 A1 | 9/2010 | Gunther et al. | |
| 2012/0078261 A1 | 3/2012 | Kecman et al. | |
| 2013/0023883 A1 | 1/2013 | Wright et al. | |
| 2013/0023890 A1 | 1/2013 | Kecman et al. | |
| 2013/0030443 A1 | 1/2013 | Wright et al. | |
| 2013/0030539 A1 | 1/2013 | Wright et al. | |
| 2013/0035693 A1 | 2/2013 | Wright et al. | |
| 2013/0079787 A1 | 3/2013 | Spencer Jones et al. | |
| 2013/0079788 A1 | 3/2013 | Spencer Jones et al. | |
| 2013/0079789 A1 | 3/2013 | Randle et al. | |
| 2013/0211410 A1 | 8/2013 | Landes et al. | |
| 2014/0094818 A1 | 4/2014 | Wallace et al. | |

FOREIGN PATENT DOCUMENTS

| | | |
|---|---|---|
| CN | 101522144 A | 9/2009 |
| CN | 101617967 A | 1/2010 |
| CN | 201814648 U | 5/2011 |
| EP | 791335 A1 | 8/1997 |
| EP | 992222 A2 | 4/2000 |
| EP | 1723916 B1 | 7/2008 |
| EP | 1967143 A2 | 9/2008 |
| EP | 2039304 | 3/2009 |
| EP | 2574314 A1 | 4/2013 |
| FR | 2737848 A1 | 2/1997 |
| GB | 2433695 A | 7/2007 |
| GB | 2433698 A | 7/2007 |
| WO | 9945856 A1 | 9/1999 |
| WO | 9965403 | 12/1999 |
| WO | 03071961 A1 | 9/2003 |
| WO | 2005110249 A1 | 11/2005 |
| WO | 2006027098 A1 | 3/2006 |

(56) References Cited

FOREIGN PATENT DOCUMENTS

| WO | 2008112996 A1 | 9/2008 |
|----|---------------|--------|
| WO | 2013003730 A1 | 1/2013 |

OTHER PUBLICATIONS

Depuy International, Ltd., PFC Sigma Rotating Platform Knee System With Mbttray, Surgical Technique Brochure, 2003 (43 Pages), Cat. No. 9068-96-000, Depuy International, Ltd., Leeds, England.

Depuy Orthopaedics, Inc., LCS High Performance Instruments, Surgical Technique Guide, 2008, (44 Pages), Pub. No. 0612-85-506, Depuy Orthopaedics, Inc., Warsaw, IN.

Depuy Orthopaedics, Inc. Sigma High Performance Instruments, Classic Surgical Technique, 2010, (52 Pages), Pub. No. 0612-89-510, Depuy Orthopaedics, Inc., Warsaw, IN.

Depuy Orthopaedics. Inc., Sigma High Performance Ins 1 Ruments. Design Rationale, 2007 (12 Pages), Pub. No. 0612-54-506 (Rev. 2), Depuy Orthopaedics, Inc., Warsaw, IN.

European Search Report, European Pat. App. No. 11175824.9-2310, dated Dec. 16, 2011 (7 Pages).

European Search Report, European Pat, App. No. 12191753.8-2310, dated Jan. 3, 2013 (6 Pages).

European Search Report for European Application No. 12174683.8-2310, dated Sep. 3, 2012, 6 pages.

European Search Report for European Application No. 12174682.0-2310, dated Sep. 5, 2012, 6 pages.

International Search Report, International Application No. PCT/US12/44947, dated Oct. 12, 2012, 3 pages.

European Search Report for European Application No. 12186675.0-2310, dated Dec. 12, 2012, 7 pages.

European Search Report for European Application No. 12186700.6-2310, dated Dec. 13, 2012, 8 pages.

European Search Report for European Application No. 12186728.7-2310, dated Dec. 14, 2012, 8 pages.

Extended European Search Report. European Application No. 16160477.2-1654, dated May 11, 2016, 8 pages.

European search report for EPO Appp No. 13186401.9-1654, dated Jan. 17, 2014, 7 pages.

European search report for EPO App. No. 13186416.7-1654, dated Dec. 6, 2013, 7 pages.

* cited by examiner

POLYMER 4-IN-2 FEMORAL CUTTING INSTRUMENT HAVING SEPARABLE A/P AND CHAMFER CUTTING BLOCKS

TECHNICAL FIELD

The present disclosure relates generally to orthopaedic surgical instruments and, more particularly, to surgical instruments used to resect a patient's bone.

BACKGROUND

Joint arthroplasty is a well-known surgical procedure by which a diseased and/or damaged natural joint is replaced by a prosthetic joint. Typical artificial joints include knee prostheses, hip prostheses, shoulder prostheses, ankle prostheses, and wrist prostheses, among others. To facilitate the replacement of the natural joint with the prosthesis, orthopaedic surgeons use a variety of orthopaedic surgical instruments such as, for example, saws, drills, reamers, rasps, broaches, cutting blocks, drill guides, milling guides, and other surgical instruments.

SUMMARY

According to one aspect of the disclosure, an orthopaedic surgical instrument includes an A/P femoral cutting block having an anterior cutting surface, a posterior cutting surface, a chamfer access window positioned between the anterior cutting surface and the posterior cutting surface, and an interference-fit connector. The orthopaedic surgical instrument also includes a chamfer femoral cutting block having a wedge-shaped chamfer cutting surface positioned in the chamfer access cutting window, and an interference-fit connector connected to the interference-connector of the A/P femoral cutting block so as to removably secure the chamfer femoral cutting block to the A/P femoral cutting block.

The interference-fit connector of the chamfer femoral cutting block may be embodied as a female connector having an elongated bore formed therein, with the interference-fit connector of the A/P femoral cutting block being embodied as a male connector having an elongated boss that is received into the elongated bore of the female connector of the chamfer femoral cutting block.

A distal end of the elongated boss of the male connector of the A/P femoral cutting may include a number of crush ribs.

The elongated boss may have a bore formed therethrough, with the bore of the elongated boss of the male connector of the A/P femoral cutting block being aligned with the elongated bore of the female connector of the chamfer femoral cutting block so as to define a pin guide bore.

The chamfer femoral cutting block may also have a lateral handle secured to a lateral end of the wedge-shaped cutting surface, with the lateral handle extending outwardly away from a lateral-most edge of the A/P femoral cutting block. The chamfer femoral cutting block may also include a medial handle secured to a medial end of the wedge-shaped cutting surface, with the medial handle extending outwardly away from a medial-most edge of the A/P femoral cutting block.

Both the A/P femoral cutting block and the chamfer femoral cutting block may be embodied as polymer cutting blocks. The orthopaedic surgical instrument may also include a metallic anterior cutting guide secured to the anterior cutting surface, a metallic posterior cutting guide secured to the posterior cutting surface, and a metallic chamfer cutting guide secured to the chamfer cutting surface.

The chamfer femoral cutting block may also include an outer surface, with the wedge-shaped cutting surface being defined in the outer surface. The chamfer femoral cutting block may also include a bone-engaging surface opposite the outer surface, with a number of spikes extending outwardly away from the bone-engaging surface.

According to another aspect, an orthopaedic surgical instrument includes a polymer A/P femoral cutting block having an anterior cutting surface and a posterior cutting surface. The instrument also includes a metallic anterior cutting guide secured to the anterior cutting surface and a metallic posterior cutting guide secured to the posterior cutting surface. The instrument further includes a polymer chamfer femoral cutting block removably secured to the polymer A/P femoral cutting block. The polymer femoral cutting block has a wedge-shaped chamfer cutting surface positioned in the chamfer access cutting window. The polymer femoral cutting block also includes a lateral handle secured to a lateral end of the wedge-shaped cutting surface, with the lateral handle extending outwardly away from a lateral-most edge of the A/P femoral cutting block, and a medial handle secured to a medial end of the wedge-shaped cutting surface, with the medial handle extending outwardly away from a medial-most edge of the A/P femoral cutting block. The instrument also includes a metallic chamfer cutting guide secured to the chamfer cutting surface.

The polymer A/P femoral cutting block further has an interference-fit connector, and the polymer chamfer cutting block further has an interference-fit connector connected to the interference-connector of the A/P femoral cutting block so as to removably secure the chamfer femoral cutting block to the A/P femoral cutting block.

The interference-fit connector of the chamfer femoral cutting block may be embodied as a female connector having an elongated bore formed therein, with the interference-fit connector of the A/P femoral cutting block being embodied as a male connector having an elongated boss that is received into the elongated bore of the female connector of the chamfer femoral cutting block.

A distal end of the elongated boss of the male connector of the A/P femoral cutting may include a number of crush ribs.

The elongated boss may have a bore formed therethrough, with the bore of the elongated boss of the male connector of the A/P femoral cutting block being aligned with the elongated bore of the female connector of the chamfer femoral cutting block so as to define a pin guide bore.

The chamfer femoral cutting block may also include an outer surface, with the wedge-shaped cutting surface being defined in the outer surface. The chamfer femoral cutting block may also include a bone-engaging surface opposite the outer surface, with a number of spikes extending outwardly away from the bone-engaging surface.

According to another aspect, a method of resecting a distal end of a patient's femur during performance of a knee replacement procedure includes securing an orthopaedic surgical instrument to the distal end of the patient's femur, with the orthopaedic surgical instrument having an A/P femoral cutting block and a chamfer femoral cutting block removably secured to the A/P cutting block. The method also includes performing anterior and posterior cuts on the distal end of the patient's femur by use of the A/P femoral cutting block, and then removing the A/P femoral cutting block from the chamfer femoral cutting block such that the chamfer femoral cutting block remains secured to the distal end of the patient's femur. The method also includes performing chamfer cuts on the distal end of the patient's femur by use of the chamfer femoral cutting block.

The A/P femoral cutting block may be removed from the chamfer femoral cutting block by impacting the chamfer femoral cutting block so as to separate the femoral cutting block from the chamfer femoral cutting block.

Impacting the chamfer femoral cutting block may also drive a number of spikes of the chamfer femoral cutting block into the distal end of the patient's femur.

An interference-fit connection may be separated during removal of the A/P femoral cutting block from the chamfer femoral cutting block.

The A/P femoral cutting block is removed from a pair of surgical pins during separation from the chamfer femoral cutting block, while the chamfer femoral cutting block remains on the pair of surgical pins.

BRIEF DESCRIPTION OF THE DRAWINGS

The detailed description particularly refers to the following figures, in which.

DETAILED DESCRIPTION OF THE DRAWINGS

Figure 1:
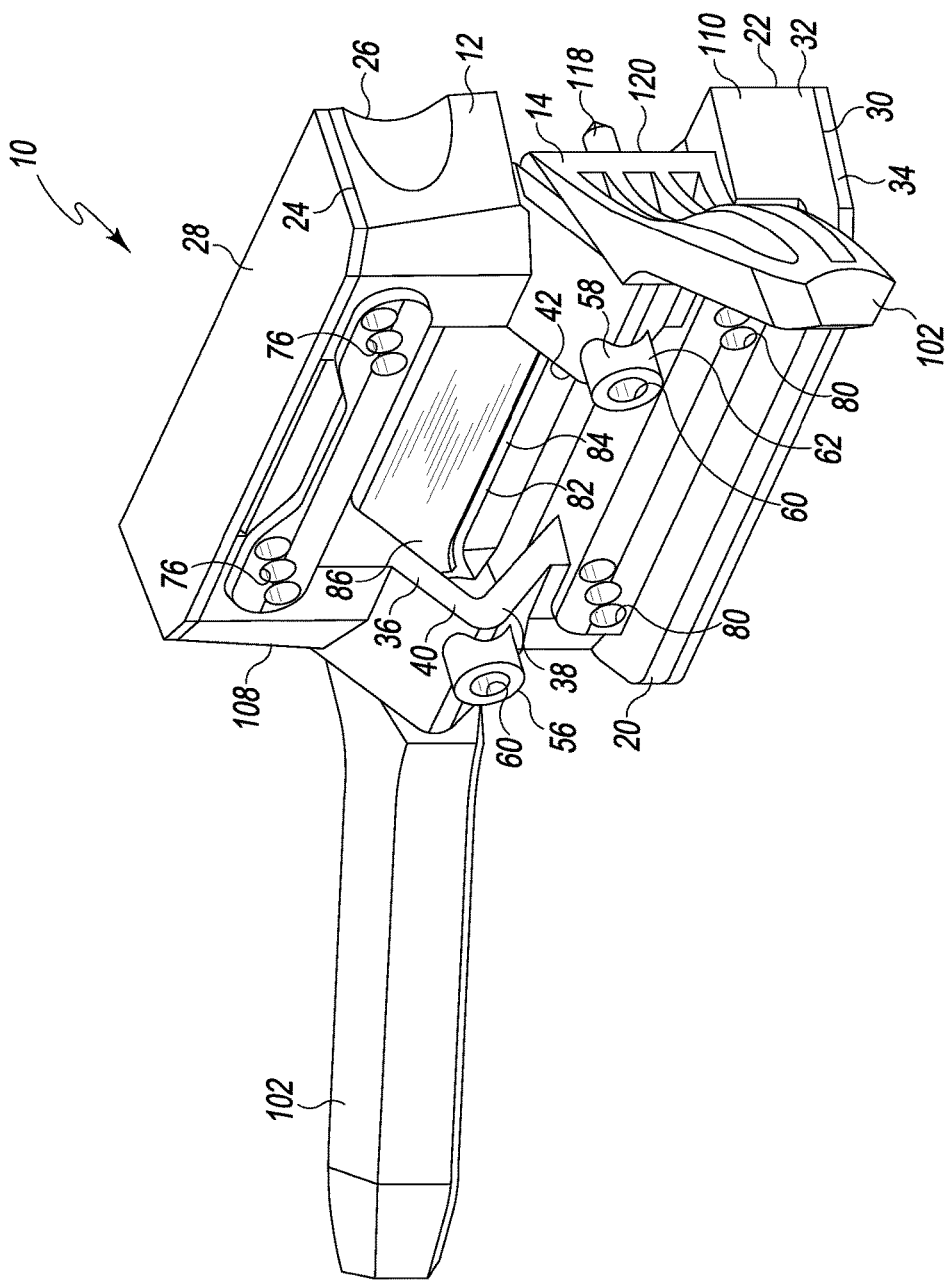
FIG. 1 is a perspective view of an orthopaedic surgical instrument.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring to FIGS. 1-6, one embodiment of an orthopaedic surgical instrument 10 for resecting the distal end of a patient's femur during a knee replacement surgery is shown. In the illustrative embodiment described herein, the orthopaedic surgical instrument 10 is embodied as a single use orthopaedic surgical instrument. As its name implies, the single use orthopaedic surgical instrument 10 is intended to be disposed of after use in a single orthopaedic procedure. In the illustrative embodiment described herein, the orthopaedic surgical instrument 10 is embodied as a single use 4-in-2 surgical instrument having an A/P femoral cutting block 12 for use by the surgeon in performing the anterior and posterior cuts in the patient's distal femur, along with a separable chamfer cutting block 14 for use by the surgeon in performing the two chamfer cuts in the patient's distal femur. In other words, the two cutting blocks 12, 14 of the 4-in-2 orthopaedic surgical instrument 10 are used to perform four cuts on the patient's distal femur—an anterior cut, a posterior cut, and two chamfer cuts.

As single use instruments, the A/P femoral cutting block 12 and the chamfer femoral cutting block 14 may be formed from polymeric materials such as, for example, polyamide, polyphenylsulfone, or polyketone. In such an embodiment, the surfaces used to guide surgical instruments such as cutting guide surfaces and bushings for guiding drills and surgical pins are formed from a metallic material such as, for example, steel, titanium alloy, or cobalt chromium alloy. Such use of metallic components or "inserts" prevents the surgical tools from coming into contact with the polymeric materials of the instrument's blocks.

The metallic components described herein may be secured to the polymer cutting blocks in a number of different manners. For example, the metallic components may be overmolded to the polymer cutting blocks or otherwise secured to it as part of the molding process of the blocks. The metallic components may also be welded to the cutting blocks or secured to them with an adhesive. Other methods of securing the metallic components may also be employed.

Figure 2:
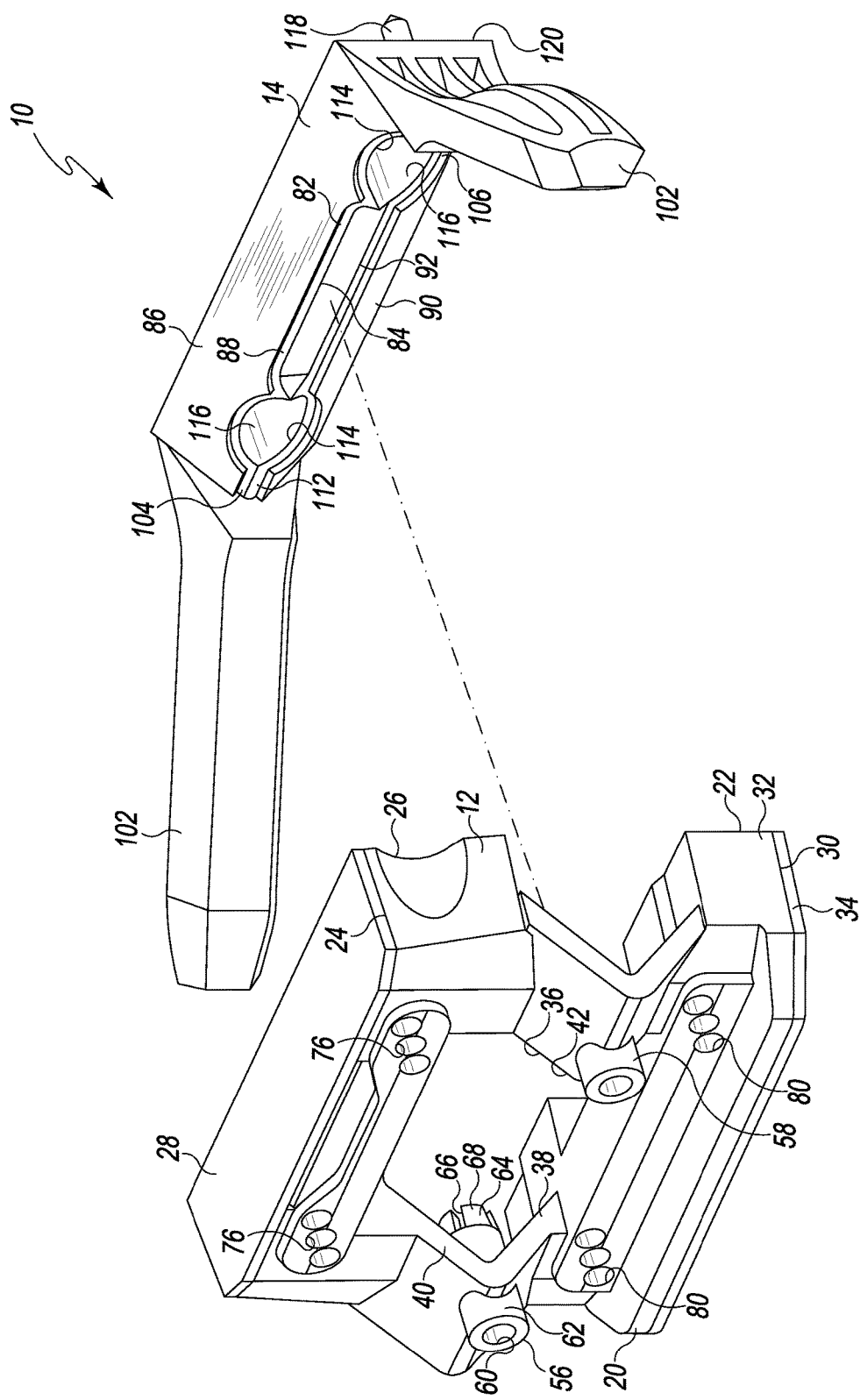
FIG. 2 is a view similar to FIG. 1, but showing the chamfer femoral cutting block separated from the A/P femoral cutting block.

The A/P femoral cutting block 12 includes an outer surface 20 and a bone-engaging surface 22 positioned opposite the outer surface 20. The A/P femoral cutting block 12 has an anterior cutting surface 24 formed on its anterior end 26. The anterior cutting surface 24 is an elongated surface extending in the medial/lateral direction. The anterior cutting surface 24 extends through the entire thickness of the A/P femoral cutting block 12—that is, the anterior cutting surface 24 extends from the cutting block's outer surface 20 to its bone-engaging surface 22. As can be seen in FIGS. 1 and 2, a metallic anterior cutting guide 28 is secured to the anterior cutting surface 24 of the polymer A/P femoral cutting block 12. The anterior cutting guide 28 lines the anterior cutting surface 24 and is embodied as a non-captured cutting guide (i.e., it is not closed on all sides). The anterior cutting guide 28 is sized and shaped to support and guide the blade (see FIG. 10) of a surgical saw or other cutting instrument and orient the blade to resect the anterior surface of the patient's femur during an orthopaedic surgical procedure.

The A/P femoral cutting block 12 has a posterior cutting surface 30 formed near its posterior end 32. The posterior cutting surface 30 is an elongated surface extending in the medial/lateral direction. The posterior cutting surface 30 extends the entire thickness of the A/P femoral cutting block 12—that is, it extends from the cutting block's outer surface 20 to its bone-engaging surface 22. As can be seen in FIG. 1, a metallic posterior cutting guide 34 is secured to the posterior cutting surface 30 of the polymer A/P femoral cutting block 12. The posterior cutting guide 34 is sized and shaped to support and guide the blade (see FIG. 10) of a surgical saw or other cutting instrument and orient the blade to resect the posterior surface of the patient's femur during an orthopaedic surgical procedure. In the illustrative embodiment described herein, the posterior cutting guide 34 is embodied as a non-captured cutting guide.

The A/P femoral cutting block 12 has an chamfer access window 36 formed near its middle. Specifically, the chamfer access window 36 is located posteriorly of the anterior cutting surface 24 and anteriorly of the posterior cutting surface 30. The chamfer access window 36 is an elongated opening extending in the medial/lateral direction. The chamfer access window 36 extends through the entire thickness of the A/P femoral cutting block 12—that is, it extends from the cutting block's outer surface 20 to its bone-engaging surface 22 and, as a result, opens to both surfaces. The chamfer access window 36 is defined by a sidewall 38 of the A/P cutting block 12. As can be seen in FIGS. 1 and 2, the medial edge 40 and the lateral edge 42 of the sidewall 38 are V-shaped, with the "point" of the V-shaped edges 40, 42 being defined in the outer surface 20 of the A/P femoral cutting block 12. Such a configuration allows the wedge-shaped cutting surface (described below) of the chamfer femoral cutting block 14 to nest within the chamfer access window 36.

Figure 5:
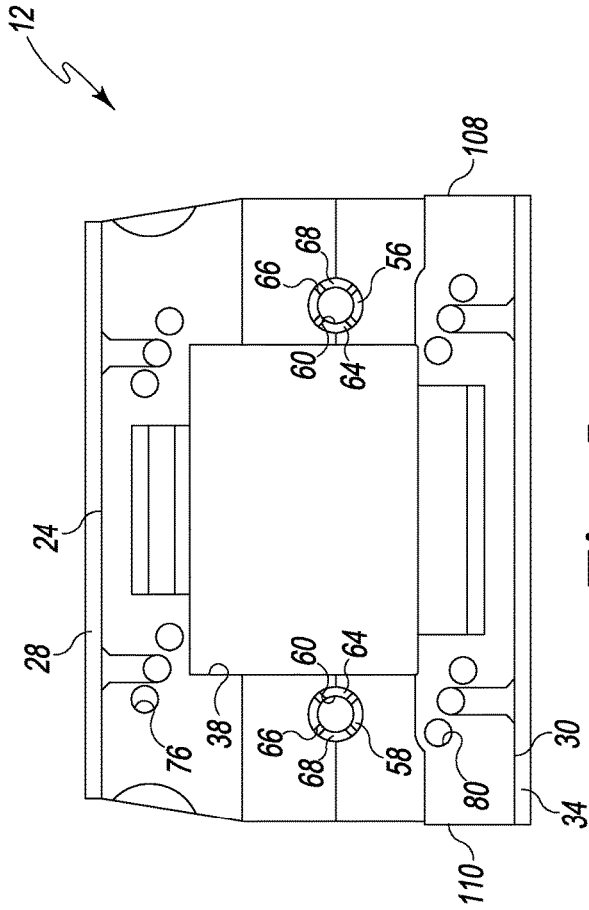
FIG. 5 is an elevation view of the bone-engaging surface of the A/P femoral cutting block of the orthopaedic surgical instrument of FIG. 1.

The A/P femoral cutting block 12 has a pair of elongated bosses 56, 58 formed therein. The medial boss 56 is positioned near the medial side of the chamfer access window 36, with the lateral boss 58 being positioned near the lateral side of the chamfer access window 36. The bosses 56, 58 are cylindrically-shaped and each have an elongated bore 60 extending therethrough. As can be seen in FIG. 1, one end 62 of the bosses 56, 58 is positioned on the outer surface 20 of the A/P femoral cutting block 12. As can be seen in FIGS. 2 and 5, the opposite, distal end 64 of each of the bosses 56, 58 extends outwardly away from the V-shaped portion of the block's bone-engaging side 22. A number of slits 66 are formed in the distal ends 64 of the bosses 56, 58 so as to form a number of collapsible flanges or crush ribs 68. As will be described in more detail below, such crush ribs 68 define an illustrative male connector for removably securing the A/P femoral cutting block 12 to the chamfer femoral cutting block 14.

The A/P femoral cutting block 12 has a plurality of guide holes 76 defined therein that are sized to receive a pair of fixation or guide pins 78. The holes 76 are positioned between the anterior cutting surface 24 and the chamfer access window 36 and extend between the outer surface 20 and the bone-engaging surface 22 of the cutting block 12. The holes 76 are arranged in a staggered pattern to permit the surgeon to change the position of the cutting block 12 on the patient's femur without having to remove the fixation pins 78, as described in greater detail below.

The A/P femoral cutting block 12 also includes another plurality of guide holes 80 positioned between the chamfer cutting 36 and the posterior cutting surface 30. Each guide hole 80 is sized to receive one of the fixation pins 78 in a similar manner to the guide holes 76 and thereby extends between the outer surface 20 and the bone-engaging surface 22 of the cutting block 12. Like the guide holes 76, the guide holes 80 are arranged in a staggered pattern to permit the surgeon to change the position of the cutting block 12 on the patient's femur without having to remove the fixation pins 78.

Figure 4:
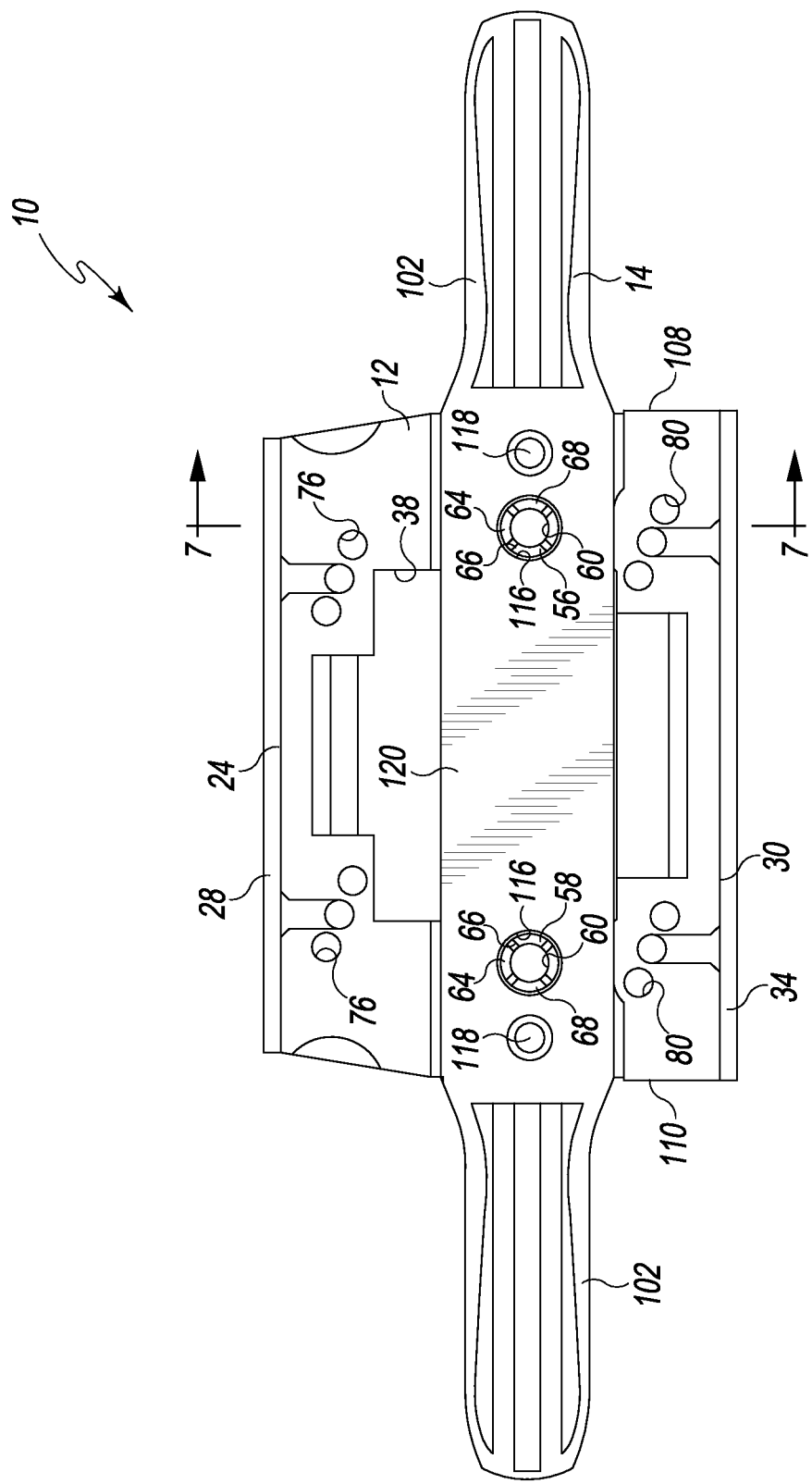
FIG. 4 is an elevation view showing the bone-engaging surface of the orthopaedic surgical instrument of FIG. 1.
Figure 12:
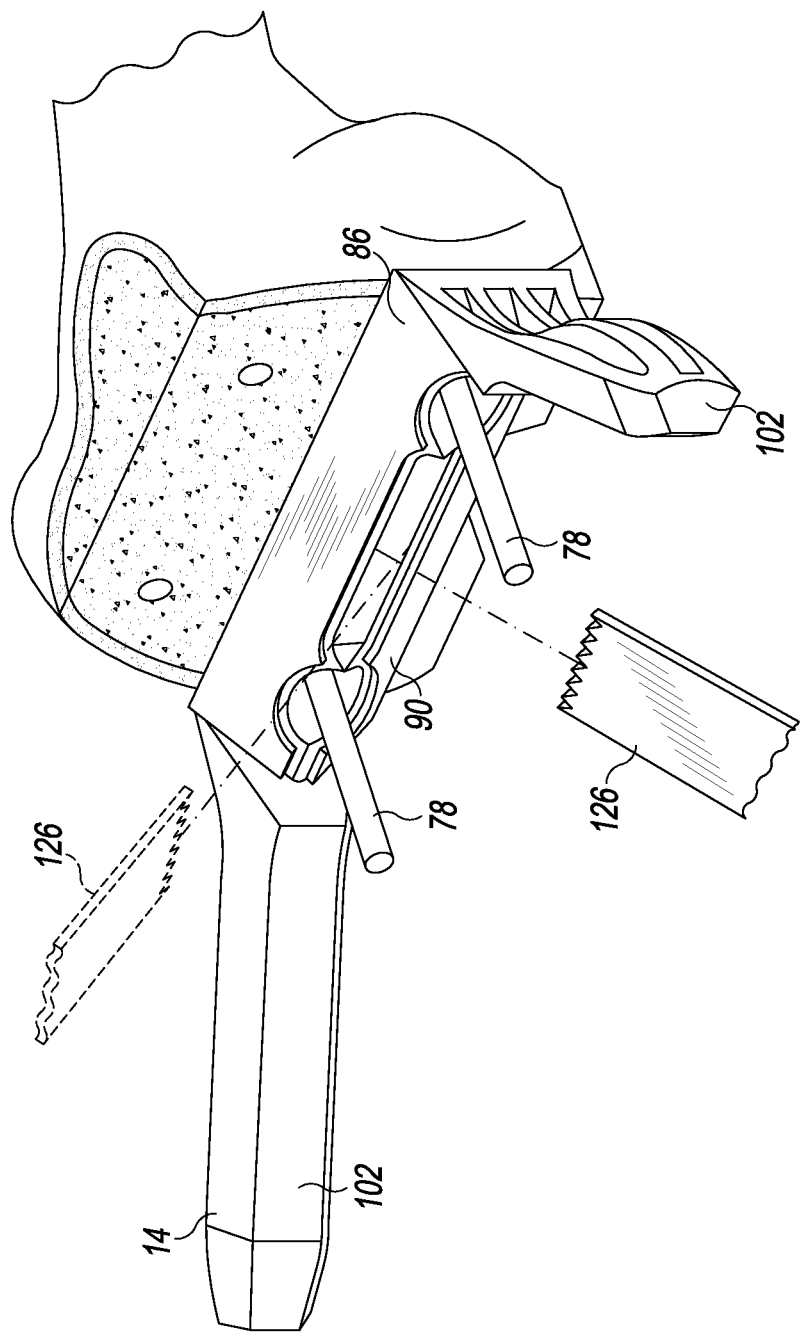
FIG. 12 is a view similar to FIG. 11, but showing the chamfer femoral cutting block of the orthopaedic surgical instrument of FIG. 1 being used to perform the chamfer cuts on the distal end of the patient's femur.

As can be seen best in FIGS. 2 and 4, the chamfer femoral cutting block 14 is removably secured to the bone-engaging surface 22 of the A/P femoral cutting block 12. The chamfer femoral cutting block 14 has a wedge-shaped cutting surface 82. The "leading" edge 84 of the wedge-shaped cutting surface 82 extends into the chamfer access window 36 and nests or otherwise contacts the corresponding V-shaped surfaces of the bone-engaging surface 22 of the A/P femoral cutting block 12. The chamfer femoral cutting block 14 has a metallic planar cutting guide 86 secured to the anterior surface 88 of the wedge-shaped cutting surface 82, with a metallic planar cutting guide 90 being secured to the posterior surface 92 of the wedge-shaped cutting surface 82. The planar cutting guides 86, 90 are arranged at an oblique angle relative to one another to line the wedge-shaped cutting surface 82. The longitudinal axis of the planar cutting guides 86, 90 extends in the medial/lateral direction. As shown in FIG. 12, the cutting guide 86 supports and guides a saw blade during performance of the anterior chamfer cut, with the cutting guide 90 being used to support and guide the saw blade during performance of the posterior chamfer cut.

Figure 3:
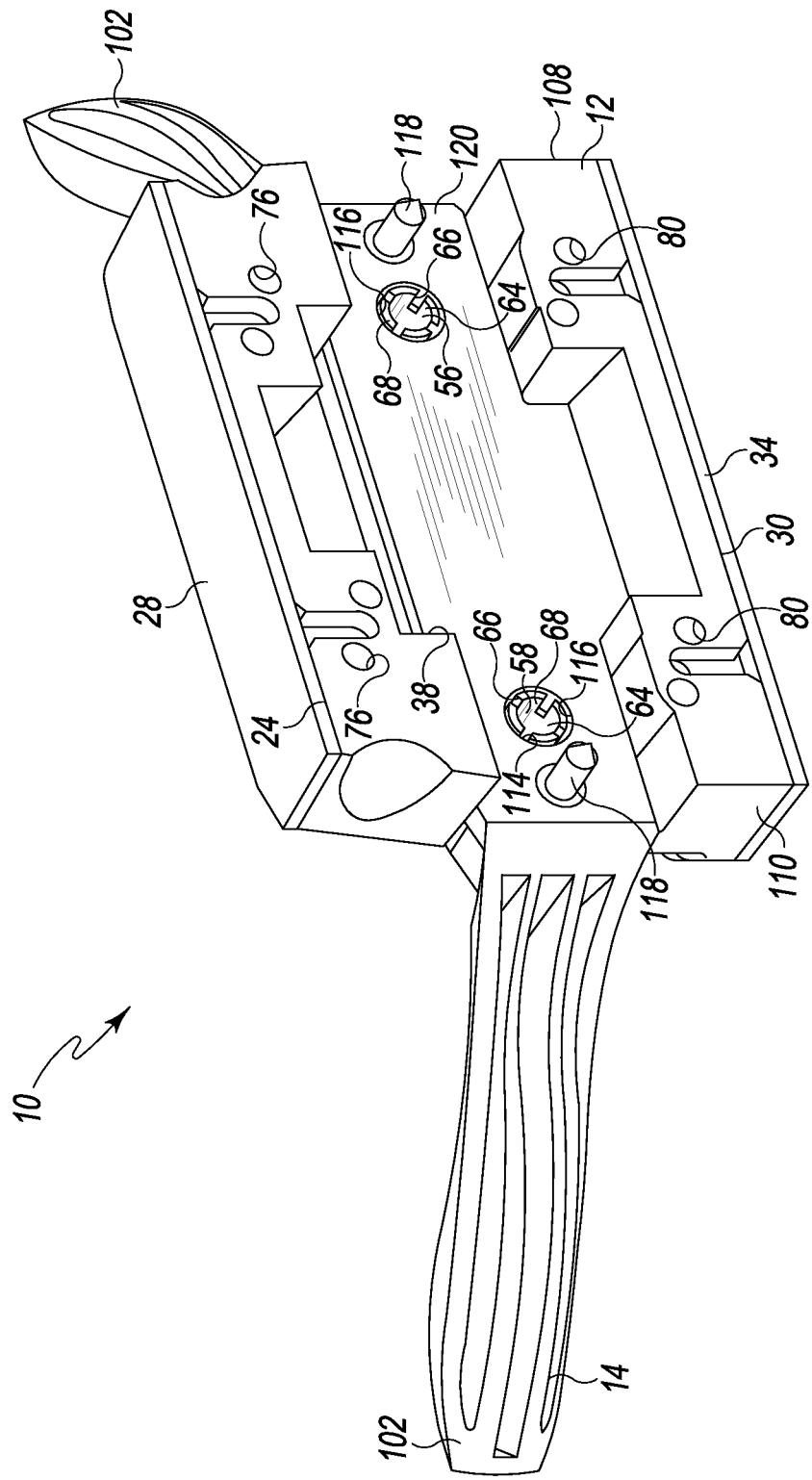
FIG. 3 is a perspective view of the bone-engaging surface of the orthopaedic surgical instrument of FIG. 1.

The chamfer femoral cutting block 14 has a pair of handles 102 extending outwardly therefrom. One of the handles 102 is secured to the medial end 104 of the wedge-shaped cutting surface 82, with the other handle 102 being secured to the opposite, lateral end 106 of the wedge-shaped cutting surface 82. As can be seen in FIGS. 1 and 3, when the A/P femoral cutting block 12 and the chamfer cutting block 14 are secured to one another, the medial handle 102 extends outwardly beyond and away from a medial-most edge 108 of the A/P femoral cutting block 12, with the lateral handle 102 extending outwardly beyond and away from a lateral-most edge 110 of the A/P femoral cutting block 12. As will be described in more detail below, a surgeon may grip the handles 102 during performance of the chamfer cuts with the chamfer femoral cutting block 14.

Figure 6:
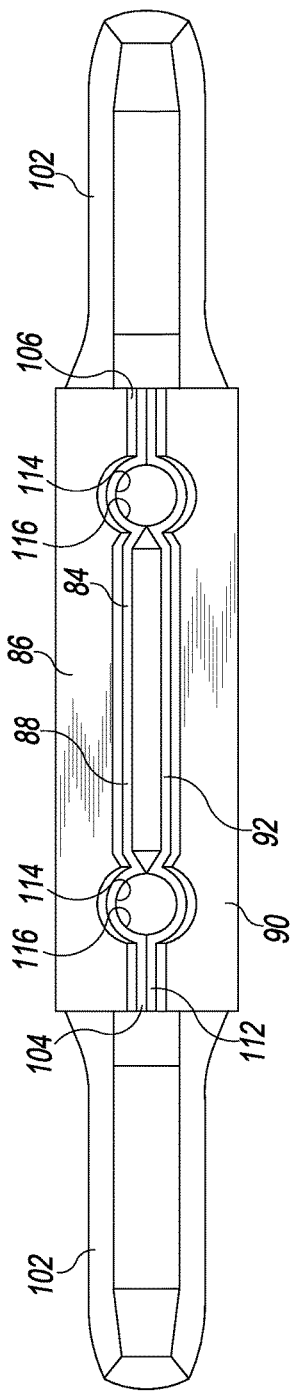
FIG. 6 is an elevation view of the outer surface of the chamfer femoral cutting block of the orthopaedic surgical instrument of FIG. 1.

As can be seen in FIGS. 2 and 6, the outer surface 112 of the chamfer femoral cutting block 14 has a pair of elongated bores 114 formed therein. The elongated bores 114 are sized and positioned to receive the distal ends 64 of the bosses 56, 58 of the A/P femoral cutting block 12. Specifically, the outer diameter of the distal ends 64 of the bosses 56, 58 is slightly larger than the inner diameter of the elongated bores 114 of the chamfer femoral cutting block 14 thereby causing the crush ribs 68 to be slightly inwardly deflected when the distal ends 64 of the bosses 56, 58 are positioned in the elongated bores 114. This creates an interference-fit connection between the A/P femoral cutting block 12 and the chamfer femoral cutting block 14. In other words, as described above, in the illustrative embodiment described herein the crush ribs 68 formed in the distal ends 64 of the bosses 56, 58 define an illustrative male interference-fit connector for removably securing the A/P femoral cutting block 12 to the chamfer femoral cutting block 14. In such an illustrative embodiment, the elongated bores 114 and the sidewalls 116 that define the bores function as the corresponding female interference-fit connector.

Figure 7:
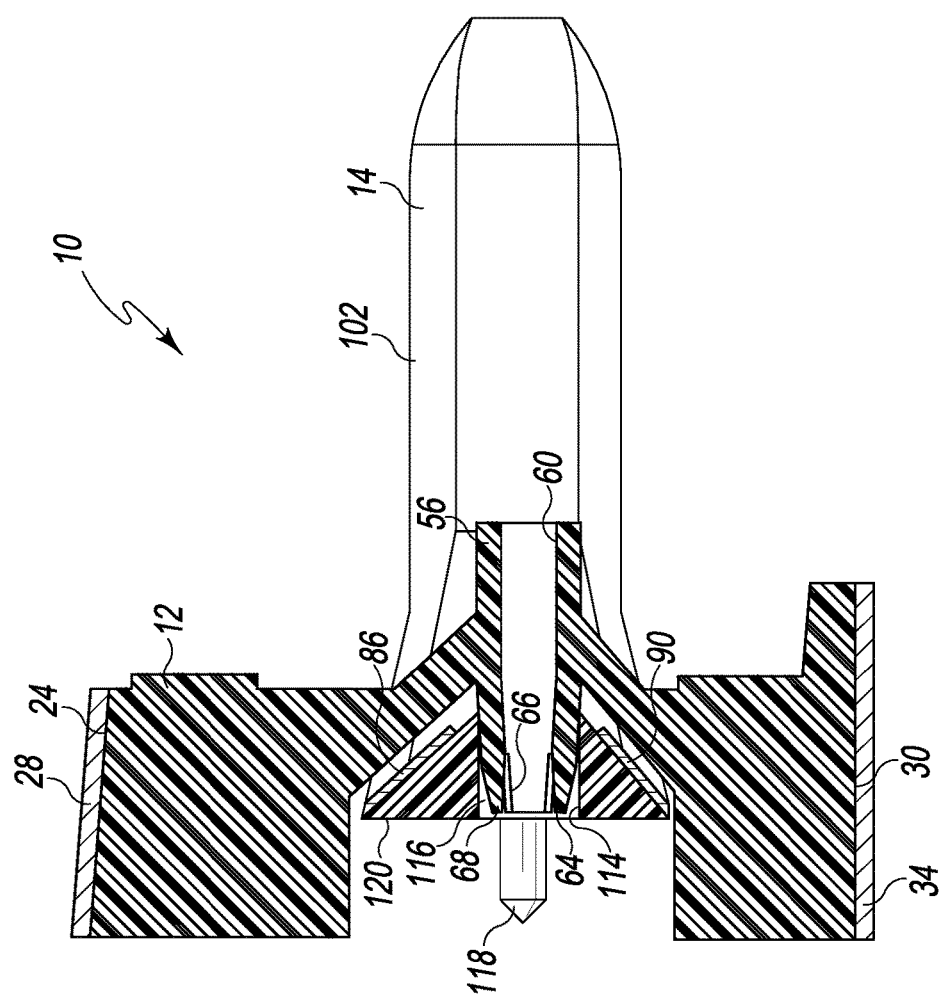
FIG. 7 is a cross section view taken along the line 7-7 of FIG. 4, as viewed in the direction of the arrows.
Figure 8:
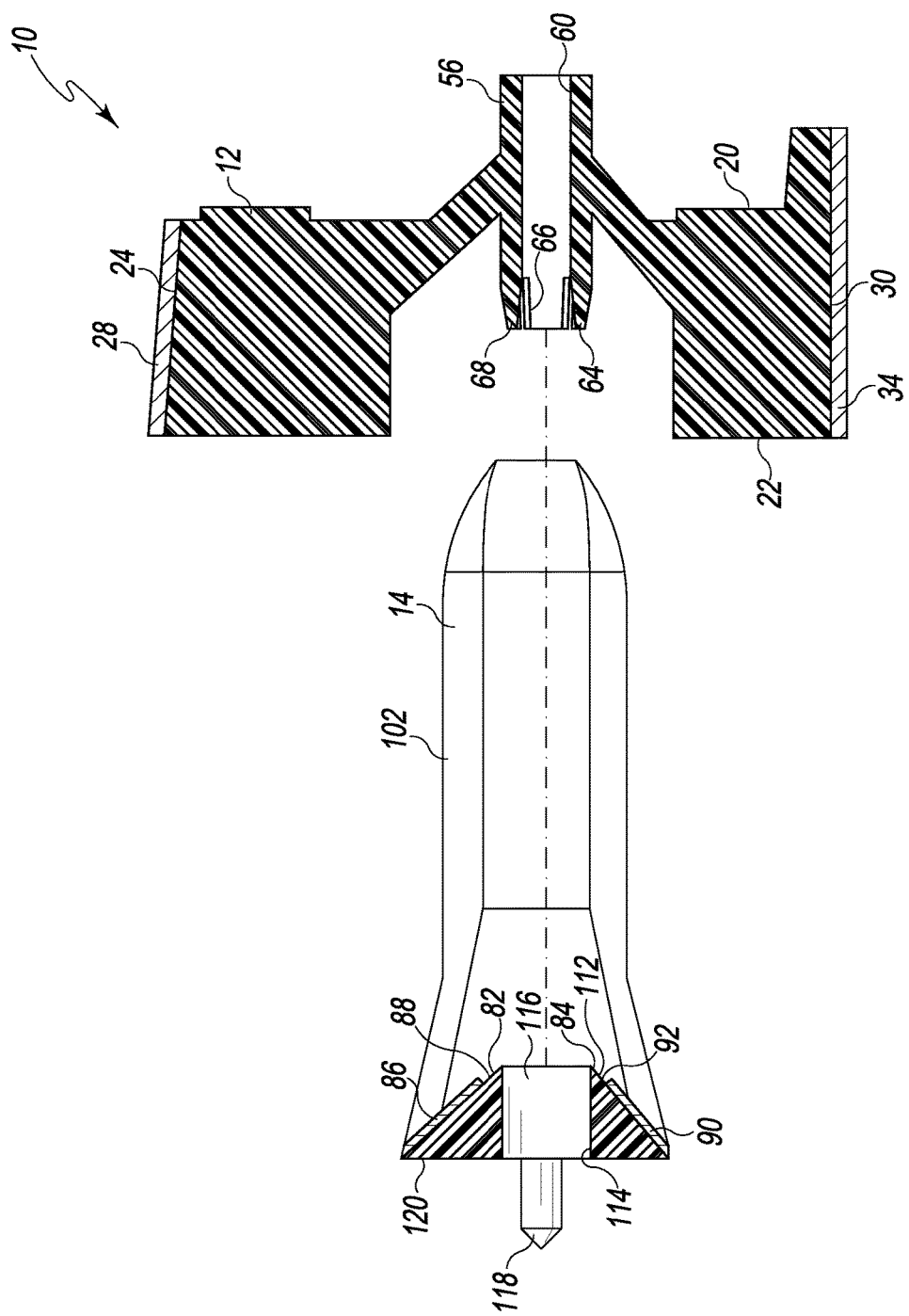
FIG. 8 is a view similar to FIG. 7, but showing the chamfer femoral cutting block separated from the A/P femoral cutting block.

As can be seen in FIGS. 7 and 8, the elongated bores 114 of the chamfer femoral cutting block 14 align with the elongated bores 60 formed in the bosses 56, 58 of the A/P femoral cutting block 12. In such a way, the two sets of bores function as a pin guide bore to receive a fixation or guide pin for pinning the orthopaedic surgical instrument 10 to the patient's distal femur (see FIG. 9), and, optionally, a drill such that the patient's femur may be pre-drilled prior to installation of the guide pins if the surgeon so desires.

As described above, the crush ribs 68 formed in the distal ends 64 of the bosses 56, 58 define an illustrative male interference-fit connector that engages the female interference-fit connector defined by the elongated bores 114 of the chamfer femoral cutting block 14 (and the sidewalls 116 that define the bores) for removably securing the A/P femoral cutting block 12 to the chamfer femoral cutting block 14. To separate the A/P femoral cutting block 12 from the chamfer femoral cutting block 14, the surgeon impacts the chamfer femoral cutting block's "leading" edge 74 of the wedge-shaped cutting surface 72 with a surgical mallet or the like. As can be seen in FIG. 1, the leading edge 74 of the wedge-shaped cutting surface 72 is accessible through the A/P femoral cutting block's chamfer access window 36 to allow for such impact with a surgical mallet. Administering the mallet impact breaks the interference fit between the two cutting blocks 12, 14 thereby causing the crush ribs 68 formed in the distal ends 64 of the bosses 56, 58 to be removed from the elongated bores 114 of the chamfer femoral cutting block 14. Such an impact also drives a pair of spikes 118 extending outwardly from the bone-engaging surface 120 of the chamfer femoral cutting block 14 into the bone tissue of the patient's distal femur. Once separated by the surgeon's impact, the A/P femoral cutting block 12 may be removed from the chamfer femoral cutting block 14.

It should be appreciated that other types of interference-fit connectors may be used in lieu of the crushed ribs arrangement described herein. The embodiment described herein is illustrative in nature and many other interference-fit arrangements, such as snap-fit arrangements and the like, may be used. Use of the interference-fit connectors allows the two blocks 12, 14 to be provided as a single, pre-installed instrument with both blocks 12, 14 being installed during performance of the anterior and posterior cuts by use of the A/P femoral cutting block 12, while also allowing for relative easy removal of the A/P femoral cutting block 12 during use of the chamfer cutting block 14 to perform the chamfer cuts. Such a pre-installed instrument allows for ease of use and improved alignment of the anterior and posterior cuts with the chamfer cuts.

In operation, the surgeon may utilize the orthopaedic surgical instrument 10 to prepare the distal end 16 of the patient's femur 18 to receive a prosthetic femoral component. To do so, the surgeon may secure the orthopaedic surgical instrument 10 to the patient's femur 18 and thereafter use the metallic cutting guides of the instrument 10 to guide a cutting saw blade in making a series of four resections of the distal end 16 of the patient's femur 18.

Figure 9:
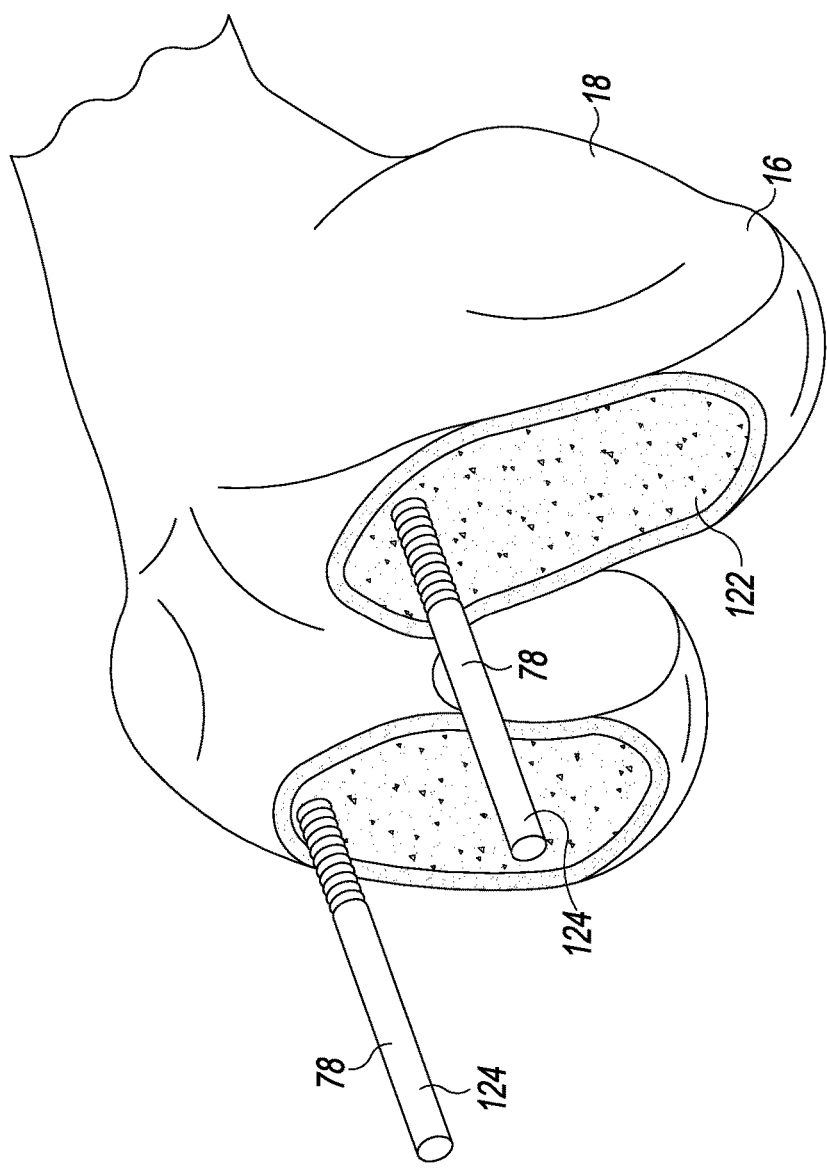
FIG. 9 is a perspective view showing a pair of fixation pins secured to a distal end of a patient's femur.

During an orthopaedic surgical procedure, the surgeon may first resect the distal end 16 of the patient's femur 18 to create a surgically-prepared distal surface 122. The surgeon may then secure a pair of fixation pins 78 to the surgically-prepared distal surface 122 of the patient's femur 18, as shown in FIG. 9. To do so, the surgeon may size the patient's femur 18 for the prosthetic femoral component and set the femoral rotation. One exemplary procedure for locating fixation pins during a femoral sizing and rotation setting procedure is described in the SIGMA® Fixed Reference Surgical Technique by DePuy Orthopaedics, Inc. (2010), which is expressly incorporated herein by reference. After sizing the femoral component and setting the rotation, the surgeon may attach the fixation pins 78 to the surgically-prepared distal surface 122 of the patient's femur 18.

Figure 10:
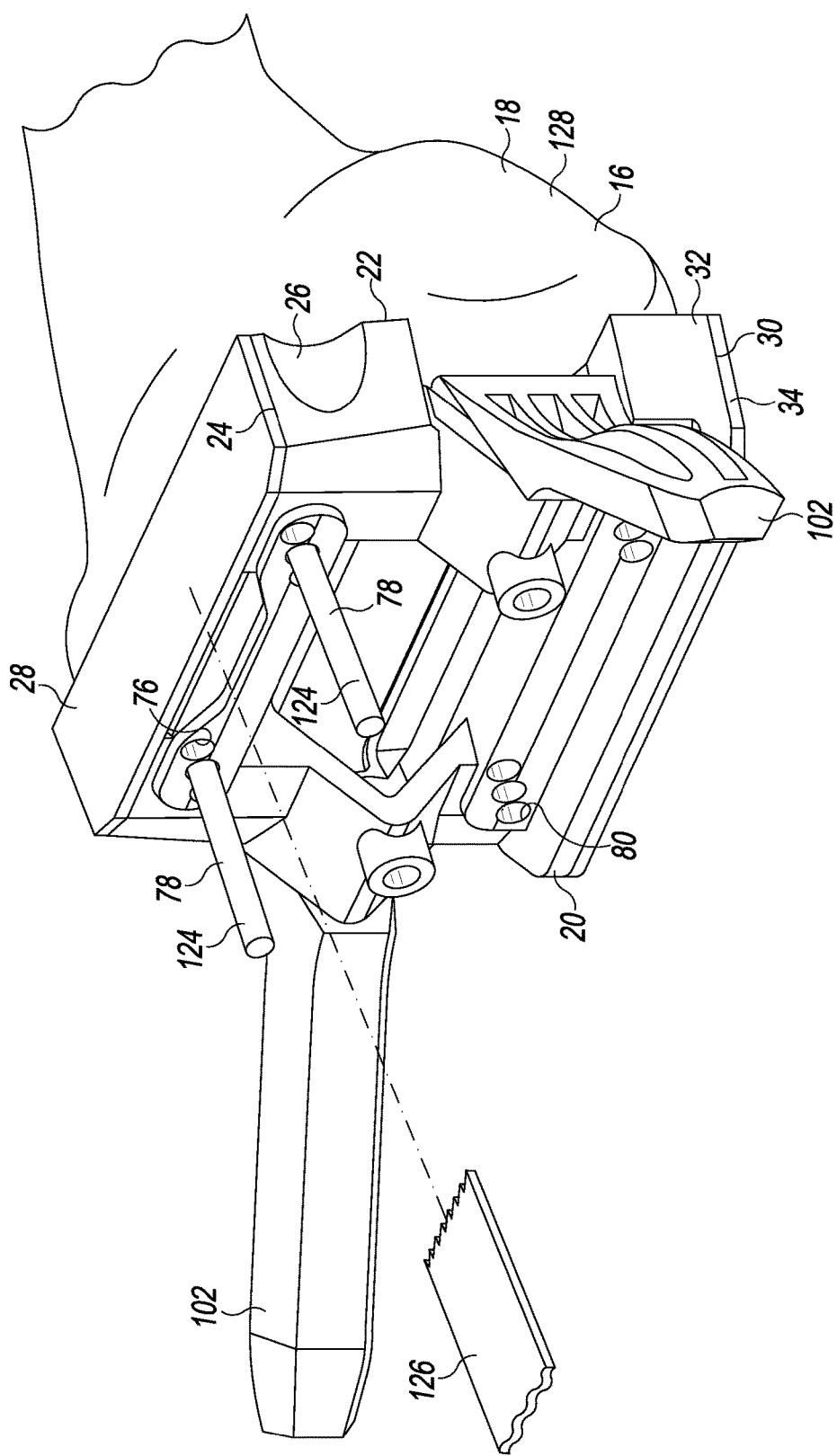
FIG. 10 is a view similar to FIG. 9, but showing the A/P femoral cutting block of the orthopaedic surgical instrument of FIG. 1 being used to perform the anterior and posterior cuts on the distal end of the patient's femur.

After attaching the fixation pins 78, the surgeon may position the orthopaedic surgical instrument 10 (including both the A/P femoral cutting block 12 and the chamfer femoral cutting block 14) on the surgically-prepared distal surface 122 of the patient's femur 18. To do so, the surgeon may align the shafts 124 of the fixation pins 78 with a pair of the guide holes 76 of the A/P femoral cutting block 12. The surgeon may then advance the A/P femoral cutting block 12 (and hence the chamfer femoral cutting block secured thereto) over the shafts 124 in a direction toward the surgically-prepared distal surface 122 of the patient's femur 18. The bone-engaging surface 22 of the A/P femoral cutting block 12 contacts the surgically-prepared distal surface 122 when the instrument 10 is positioned on the distal end 16 of the patient's femur 18, as shown in FIG. 10. If the surgeon desires to relocate the A/P femoral cutting block 12, the surgeon may utilize another combination of guide holes 76 to change the position of the cutting block 12 on the patient's femur 18. If additional fixation is necessary, the surgeon may insert additional fixation pins 78 through the guide holes 80 defined in the A/P femoral cutting block 12.

Once installed in such a manner, the surgeon may use the A/P femoral cutting block 12 to make a number of resections of the distal end 16 of the patient's femur 18. For example, as shown in FIG. 10, the anterior cutting guide 28 defines a resection plane that extends through the distal end 16 of the patient's femur 18. The surgeon may advance a cutting tool, such as, for example, a surgical cutting saw 126 along the anterior cutting guide 28 to engage the patient's femur 18 and operate the surgical saw 96 to surgically prepare an anterior surface of the patient's femur 18 to receive the prosthetic femoral component. The surgeon may similarly use the posterior cutting guide 34 to resect the posterior condyles 128 of the patient's femur 18 and surgically prepare the posterior surfaces of the patient's femur 18 to receive the prosthetic femoral component.

Figure 11:
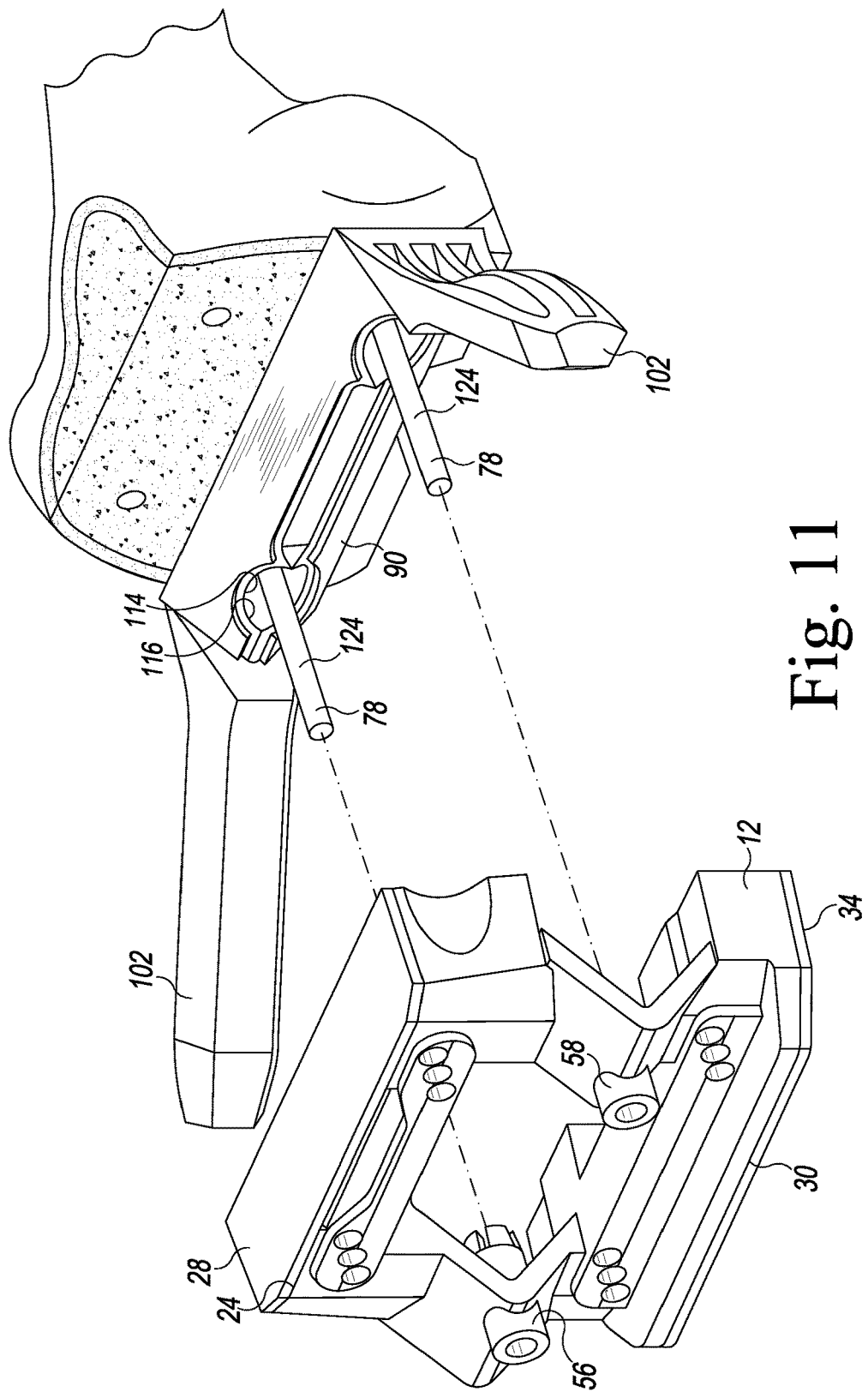
FIG. 11 is a view similar to FIG. 10, but showing the A/P femoral cutting block of the orthopaedic surgical instrument of FIG. 1 being separated from the chamfer femoral cutting block.

As shown in FIGS. 11 and 12, the surgeon may also use the orthopaedic surgical instrument 10, particularly its chamfer femoral cutting block 14, to make chamfer cuts on the patient's femur 18. To do so, the surgeon may first insert fixation pins 78 through the elongated bores 60 of the metallic bushings 56, 58. Doing so also passes the fixation pins 78 through the elongated bores 114 of the chamfer femoral cutting block 14. The surgeon may then remove any fixation pins 78 from the guide holes 76, 80 since fixation pins 78 positioned in the guide holes 76, 80 would disrupt the chamfer cutting process.

The surgeon may then impact the chamfer femoral cutting block's "leading" edge 74 of the wedge-shaped cutting surface 72 (which is accessible through the A/P femoral cutting block's chamfer access window 36) with a surgical mallet or the like. Such an impact breaks the interference fit between the two cutting blocks 12, 14 thereby causing the crush ribs 68 formed in the distal ends 64 of the bosses 56, 58 to be removed from the elongated bores 114 of the chamfer femoral cutting block 14. Such an impact also drives the chamfer femoral cutting block's spikes 118 into the bone tissue of the patient's distal femur. As shown in FIG. 11, once separated by the surgeon's mallet impact, the A/P femoral cutting block 12 may be slid along the fixation pins 78 and, as a result, removed from the chamfer femoral cutting block 14.

As shown in FIG. 12, the surgeon may then advance the surgical cutting saw 126 along the metallic cutting guide 86 to support and guide the saw 126 during performance of the anterior chamfer cut, and thereafter along the metallic cutting guide 90 to support and guide the saw 126 during performance of the posterior chamfer cut. During performance of such chamfer cuts, the surgeon may grip the handles 102 to further stabilize the cutting process.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic surgical instrument comprising:
an A/P femoral cutting block having (i) an anterior cutting surface, (ii) a posterior cutting surface, (iii) a chamfer access window positioned between the anterior cutting surface and the posterior cutting surface, and (iv) an interference-fit connector comprising a male connector having an elongated boss that extends to a distal end, the elongated boss having a bore formed therethrough and a number of crush ribs at its distal end, and
a chamfer femoral cutting block having (i) a wedge-shaped chamfer cutting surface positioned in the chamfer access window, (ii) a bone-engaging surface positioned opposite the wedge-shaped chamfer cutting surface, and (iii) a female interference-fit connector comprising a smooth inner sidewall that defines an elongated bore extending through the posterior surface,
wherein a distal end of the elongated boss of the interference-fit connector of the A/P femoral cutting block is received into the elongated bore of the female connector of the chamfer femoral cutting block so as to removably secure the chamfer femoral cutting block to the A/P femoral cutting block, and
wherein the elongated boss of the male connector of the A/P femoral cutting block is removeably positioned within the elongated bore of the female interference-fit connector of the chamfer femoral cutting block to (i) engage the crush ribs with the smooth inner sidewall of the female interference-fit connector of the chamfer femoral cutting block within the elongated bore to removably secure the chamfer femoral cutting block to the A/P femoral cutting block and (ii) align the bore of the elongated boss of the male connector of the A/P femoral cutting block with the elongated bore of the female interference-fit connector of the chamfer femoral cutting block to define a pin guide bore extending through the A/P femoral cutting block and the bone-engaging of the chamfer femoral cutting block.

2. The orthopaedic surgical instrument of claim 1, wherein the chamfer femoral cutting block further has:
a lateral handle secured to a lateral end of the wedge-shaped cutting surface, the lateral handle extending outwardly away from a lateral-most edge of the A/P femoral cutting block, and
a medial handle secured to a medial end of the wedge-shaped cutting surface, the medial handle extending outwardly away from a medial-most edge of the A/P femoral cutting block.

3. The orthopaedic surgical instrument of claim 1, wherein:
the A/P femoral cutting block comprises a polymer A/P femoral cutting block, and
the chamfer femoral cutting block comprises a polymer chamfer femoral cutting block.

4. The orthopaedic surgical instrument of claim 3, further comprising:
a metallic anterior cutting guide secured to the anterior cutting surface,
a metallic posterior cutting guide secured to the posterior cutting surface, and
a metallic chamfer cutting guide secured to the chamfer cutting surface.

5. The orthopaedic surgical instrument of claim 1, wherein the chamfer femoral cutting block further has a number of spikes extending outwardly away from the bone-engaging surface.

6. The orthopaedic surgical instrument of claim 1, further comprising a fixation pin sized to be received in, and extend through, the pin guide bore.

7. An orthopaedic surgical instrument comprising:
a polymer A/P femoral cutting block having an anterior cutting surface and a posterior cutting surface, the polymer A/P femoral cutting block having a chamfer access window positioned between the anterior cutting surface and the posterior cutting surface, the A/P femoral cutting block further having an interference-fit connector comprising a male connector having an elongated boss that extends to a distal end, the elongated boss having a bore formed therethrough and a number of crush ribs at its distal end,
a metallic anterior cutting guide secured to the anterior cutting surface,
a metallic posterior cutting guide secured to the posterior cutting surface,
a polymer chamfer femoral cutting block removably secured to the polymer A/P femoral cutting block, the polymer chamfer femoral cutting block having (i) a body including a wedge-shaped chamfer cutting surface positioned in the chamfer access window and a bone-engaging surface positioned opposite the wedge-shaped chamfer cutting surface, (ii) a lateral handle secured to a lateral end of the body, the lateral handle extending outwardly away from a lateral-most edge of the A/P femoral cutting block, (iii) a medial handle secured to a medial end of the body, the medial handle extending outwardly away from a medial-most edge of the A/P femoral cutting block, and (iv) a female interference-fit connector comprising an inner sidewall that defines an elongated bore extending through the body, wherein the distal end of the elongated boss of the A/P femoral cutting block is received into the elongated bore of the female interference-fit connector of the chamfer femoral cutting block to engage the crush ribs with the inner sidewall of the female interference-fit connector of the chamfer femoral cutting block so as to removably secure the chamfer femoral cutting block to the A/P femoral cutting block, and a metallic chamfer cutting guide secured to the chamfer cutting surface, wherein the bore of the elongated boss of the male connector of the A/P femoral cutting block is aligned with the elongated bore of the female interference-fit connector of the chamfer femoral cutting block so as to define a pin guide bore extending through the A/P femoral cutting block and the bone-engaging surface of the chamfer femoral cutting block.

8. The orthopaedic surgical instrument of claim 7, wherein the chamfer femoral cutting block further has a number of spikes extending outwardly away from the bone-engaging surface.

* * * * *